United States Patent [19]

Matsumoto et al.

[11] Patent Number: 5,606,055
[45] Date of Patent: Feb. 25, 1997

[54] ORGANIC WHITE PIGMENT

[75] Inventors: Shigekazu Matsumoto; Takao Yanagisawa, both of Osaka, Japan

[73] Assignee: Hakkol Chemical Co., Ltd., Osaka, Japan

[21] Appl. No.: 135,416

[22] Filed: Oct. 13, 1993

[30] Foreign Application Priority Data

Oct. 13, 1992 [JP] Japan ................................. 4-274370

[51] Int. Cl.$^6$ ................................................ C07D 403/12
[52] U.S. Cl. .............................. 544/83; 544/113; 544/198
[58] Field of Search .............................. 544/198, 83, 113

[56] References Cited

U.S. PATENT DOCUMENTS

| | | | |
|---|---|---|---|
| 2,544,071 | 3/1951 | Dudley | 544/198 |
| 3,309,345 | 3/1967 | Lutwack | 544/198 |
| 3,734,909 | 5/1973 | Varsanyi et al. | 544/198 |
| 3,928,344 | 12/1975 | Westlinning et al. | 544/198 |
| 4,400,505 | 8/1983 | Loffelman et al. | 544/198 |
| 4,492,643 | 1/1985 | Werle et al. | 544/198 |

OTHER PUBLICATIONS

Cram & Hammond, "Organic Chemistry" McGraw–Hill Book Co., New York (1964) 2nd Edition, pp. 565–567.
Petrou et al., Chemical Abstracts, vol. 81, entry 63590k (1974).
Cipolli et al. Chemical Abstracts; 116: 215641 (1992).
Cipolli et al, Chemical Abstracts; 115: 115737 (1991).

*Primary Examiner*—John M. Ford
*Attorney, Agent, or Firm*—Wenderoth, Lind & Ponack

[57] ABSTRACT

A novel organic white pigment which can be applied to an organic white pigment composition useful as a paper coating agent or an aqueous or oily ink or paint is provided. This organic white pigment consists of an alkylene-bismelamine derivative, represented by the following general formula (I),

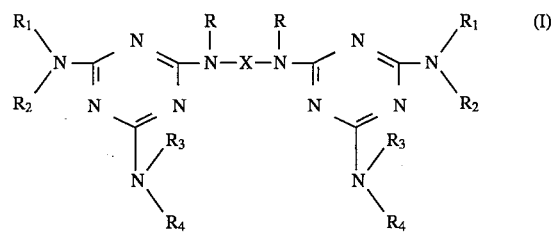

wherein R is a hydrogen atom or a lower alkyl group containing 1 to 4 carbon atoms or alicyclic group, $R_1$, $R_2$, $R_3$, and $R_4$ are respectively same or different hydrogen atoms or lower alkyl groups containing 1 to 4 carbon atoms, $R_1$ and $R_2$, or $R_3$, and $R_4$ may respectively form heterocyclic groups with nitrogen atoms and X is a lower alkylene group containing 2 to 3 carbon atoms.

4 Claims, No Drawings

ORGANIC WHITE PIGMENT

BACKGROUND OF THE INVENTION

1. Field of the Invention

This invention relates to a novel organic white pigment which can be applied to an organic white pigment composition useful as a paper coating agent or an aqueous or oily ink or paint.

2. Description of the Prior Art

Up to the present time, clay, kaolin clay, talc, calcium carbonate, zinc oxide or titanium oxide have predominantly been used, individually or in combination, as a pigment component of a white pigment.

However, when this pigment component is used for the preparation of a dispersed composition, the pigment component tends to be precipitated because of being an inorganic material having a large density and it us difficult to obtain a uniform and stable dispersed composition thereof. This is not preferable in view of the storage stability of the pigment-dispersed composition. Coating a sheet of paper with such a pigment composition, for example, naturally results in increase of the weight of the paper. In addition, such an inorganic pigment has a disadvantage that compatibility with a reagent required for the preparation of binders and other dispersed compositions is inferior.

SUMMARY OF THE INVENTION

It is an object of the present invention to provide a new organic white pigment, whereby the disadvantages of the prior art can be overcome.

It is another object of the present invention to provide an organic white pigment excellent in compatibility with surfactants, organic color pigments and other additives.

It is a further object of the present invention to provide organic pigment composition with excellent dispersion stability and storage stability.

These objects can be attained by an alkylenebismelamine derivative for an organic white pigment, represented by the following general formula (I),

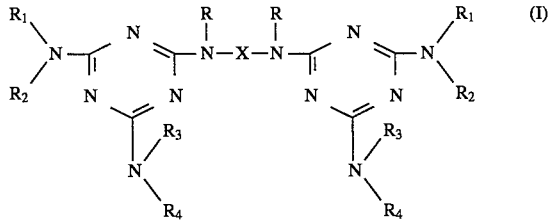

wherein R is a hydrogen atom or a lower alkyl group containing 1 to 4 carbon atoms or alicyclic group, $R_1$, $R_2$, $R_3$ and $R_4$ are respectively same or different hydrogen atoms or lower alkyl groups containing 1 to 4 carbon atoms, $R_1$, and $R_2$, or $R_3$ and $R_4$ may respectively form heterocyclic groups with nitrogen atoms and X is a lower alkylene group containing 2 to 3 carbon atoms.

DETAILED DESCRIPTION OF THE INVENTION

The inventors have made various studies to solve the problems of inorganic white pigments of the prior art, as described above, and consequently, have found that an alkylenebismelamine derivative has very excellent properties as an organic white pigment. The present invention is based on this finding.

Accordingly, the present invention provides an alkylenebismelamine derivative for an organic white pigment, represented by the foregoing General Formula (I).

The alkylenebismelamine derivative of the present invention will now be illustrated in detail. In General Formula (I), R represents a hydrogen atom or lower alkyl group containing 1 to 4 carbon atoms such as methyl, ethyl, propyl or butyl group, or an alicyclic group such as cyclohexyl group. $R_1$, $R_2$, $R_3$ and $R_4$ represent respectively same or different hydrogen atoms and lower alkyl groups containing 1 to 4 carbon atoms such as methyl, ethyl, propyl and butyl group. $R_1$ and $R_2$, or $R_3$ and $R_4$ may respectively form heterocyclic groups with nitrogen atoms, for example, piperidyl, morpholino groups, etc., and X represents a lower alkylene group containing 2 to 3 carbon atoms, for example, —$CH_2CH_2$— or —$CH_2CH_2CH_2$—.

The alkylenebismelamine derivative of the present invention, represented by General Formula (I), is a white crystal generally having a high melting point (at least 300° C.) and thus exhibits an excellent heat resistance. Furthermore, this derivative has a high degree of whiteness, good hiding property and small specific gravity because of being an organic compound, and further has a number of properties essential as a pigment component, i.e. less solubility in various solvents and good solvent resistance.

The pigment component of the present invention, i.e. lower alkylenebismelamine derivative represented by General Formula (I), can readily be prepared by the following process:

This process comprises reacting one equivalent of a cyanuric halide with four equivalents of ammonia, a lower monoalkylamine or lower dialkylamine, then reacting the resulting 2,4-diamino(di-lower monoalkylamino or di-lower dialkyl-amino)-6-halogeno-1,3,5-triazine with ½ equivalent of an alkylenediamine or substituted alkylenediamine.

Specifically, one equivalent of a cyanuric halide is dispersed in ice water with a small amount of a surfactant and maintained at 0° to 5° C. while stirring, to which an aqueous solution containing four equivalents of ammonia (alternatively, lower mono- or dialkylamine) is dropwise added. After the dropwise addition, the mixture is heated to 40° to 45° C. and reacted for about 3 hours and the thus precipitated white crystals are then filtered. The resulting cake of 2,4-diamino (or di-lower mono- or dialkylamino)-6-halogeno-1,3,5-triazine is dispersed in water, mixed with ½ equivalent of an alkylenediamine (or substituted alkylenediamine) and reacted at a temperature of 95° to 100° C. with agitation until the alkalinity disappears. While maintaining the same temperature, an aqueous solution containing two equivalents of sodium hydroxide is dropwise added thereto for about 2 hours. pH of the reaction mixture becomes about 8 and the content once becomes a transparent solution, after which white crystals are shortly precipitated. The reaction mixture is further maintained at 95° to 100° C. for about 3 hours to complete the reaction and then allowed to cool. When the temperature becomes about 50° C., the pH of the reaction mixture is adjusted to a weak alkalinity of about pH 10 and the precipitated crystals are filtered, adequately washed with water and dried.

As the cyanuric halide, there is specifically used cyanuric chloride. Examples of the amine to be reacted with the cyanuric halide include ammonia, mono-(or di-)methylamine, mono-(or di-)ethylamine, dipropylamine, dibutylamine, morpholine, piperidine, etc. As the alkylenediamine, there can preferably be used ethylenediamine, N,N'-dimethylethylenediamine, N,N'-dicyclohexylethylene-diamine, propylenediamine and the like.

For the preparation of a pigment composition, the thus obtained alkylenebismelamine derivative is used in known manner, i.e. in the form of a powder, aqueous dispersion, dispersion in a suitable organic solvent or paste. As the organic solvent, there are generally used alcohols, esters, ethers, halogen compounds, hydrocarbons, ketones and the like. Specific examples thereof are butyl alcohol, ethyl acetate, Cellosolve, trichloroethylene, xylene, turpentine oil, solvent naphtha, methyl ethyl ketone, etc.

Preparation of the pigment composition in such a form can be carried out by dry or wet process using a known finely pulverizing machine such as ball mill, sand mill, spead line mill, jet mill, etc. As occasion demands, a method is employed comprising treating a pigment component with a surfactant and water using the above described pulverizing machine to form an aqueous dispersion and then subjecting the dispersion to spray drying.

For the preparation of the dispersed composition in the above described form, a suitable surfactant is generally used. Depending on the variety of the form or the use of the composition, a suitable surfactant is mainly selected from anion type- or nonion type-surfactants. During or after the preparation of the pigment composition, the commonly used additives for such a pigment composition, for example, gelation inhibitors, protective colloid agents, preservatives and, if necessary, fluorescent whitening agents can be added thereto depending on the object of use or the form.

In addition, other organic color pigment components or pigment compositions can be added to the pigment component or pigment composition of the present invention, thereby obtaining color pigment compositions with suitable color tones and concentrations. That is, the pigment component or composition according to the present invention is useful as a base for other color pigment components or compositions.

The important feature of the white pigment composition using the alkylenebismelamine derivative of the present invention consists in that the pigment component has a small specific gravity because of being an organic material and accordingly, the weight of a paper using the same is lighter than that of a composition comprising an inorganic pigment component, resulting in lowering of the transporting or mailing cost.

Comparison of the specific gravity of an ethylenebismelamine corresponding to General Formula (I) wherein all of $R_1$, $R_2$, $R_3$ and $R_4$ are hydrogen atoms and X is —$CH_2CH_2$— with that of a known inorganic pigment component is tabulated below:

TABLE 1

| White Pigment Component | Specific Gravity |
|---|---|
| Ethylenebismelamine | 1.4 |
| Clay | 2.46–2.63 |
| Talc | 2.6–2.8 |
| Calcium Carbonate | 2.83 |
| Titanium Oxide | 3.7–3.9 |
| Zinc Oxide | 5.4–5.7 |

In this Table 1, the specific gravity of ethylenebismelamine is measured by a measurement method using a specific gravity bottle, of the solid specific gravity measurement methods according to JIS Z 8807.

The compound of General Formula (I) according to the present invention is also excellent in whiteness degree and hiding power, in particular, when used as a white pigment. For example, the foregoing ethylenebismelamine was used as a pigment component to prepare an aqueous dispersed composition (pigment component content=40 weight %, grain size=at most 5 μm ), while for comparison, calcium carbonate, clay (commercial name, HG-90) or calcined clay was used as a pigment component with the same concentration and composition to prepare comparative aqueous dispersed compositions. These aqueous dispersed compositions were subjected to coating under the following conditions:

Wire Rod: No. 14

Coating Temperature: room temperature

Drying Condition: 120° C., 1 minute and then dried to obtain black board-papers and Kinsha Paper -commercial namemade by Kinshuseishi Co., Ltd. for comparison of the degree of whiteness, thus obtaining results as shown in Table 2. In Table 2, the larger numerals show the more excellent whiteness degree.

TABLE 2

| | Degree of Whiteness | | | |
|---|---|---|---|---|
| | Black Board-Paper | | Kinsha Paper | |
| Pigment Composition | W(Lab) | WB | W(Lab) | WB |
| Ethylenebismelamine | 85.91 | 76.02 | 92.30 | 84.45 |
| Calcium Carbonate | 55.70 | 32.22 | 91.22 | 81.62 |
| Clay (HG-90) | 63.49 | 47.72 | 91.25 | 80.97 |
| Calcined Clay | 81.39 | 71.78 | 91.55 | 81.63 |
| Blank | 22.84 | 4.93 | 89.46 | 78.31 |

Herein, W(Lab) is a Hunter whiteness degree of L, a, b system and WB is a whiteness degree obtained by a reflectivity of an optical fiber from a sample, which are calculated by the following formulas 1 and 2:

$$W(Lab)=100-\{(100-L)^2+a^2+b^2\}^{1/2} \quad \text{Formula 1}$$

$$WB=Z\times0.847 \quad \text{Formula 2}$$

L, a, b are measures in the case of representing a color (whiteness degree) on three-dimensional coordinates, measured by a color difference meter, which is one of the commonly used color measurement methods. That is, when an ordinate and abscissa, vertically crossed on a same plane, are taken to define the crossed point as O and a vertical axis to the plane is taken from the crossed point O, a height from the plane is represented by L which means a lightness. a and b represent hues, a representing the hue in such a manner that the larger numeral shows a larger reddish degree in the right direction from the ordinate, i.e (+) side and a larger greenish degree in the left direction from the ordinate, i.e. (−) side, and b representing the hue in such a manner that the (+) side from the abscissa shows a yellowish degree and the (−) side from the abscissa shows a bluish degree. When the colors (whiteness degrees) of two samples are compared, therefore, the difference between their distances from the standard point on the three-dimensional coordinates means "color difference" between the samples. In the case of the whiteness degree, L is the larger, a is the larger in the (+) side and b is the larger in the (−) side, the whiteness is the larger.

z in Formula 2 (WB=Z×0.847) represents a reflectivity of an optical fiber from a sample.

The numerals in Table 2 are average values of values obtained by measuring suitable sites on the coated papers using "Color Measurement System Σ90" made by Nippon Denshoku Kogyo KK.

As is evident from Table 2, the whiteness degrees of the blackboard paper and gold sand paper coated with the pigment composition of the present invention are more excellent with respect to both W(Lab) and WB than when using the other three inorganic pigments. Thus, it is apparent the pigment composition of the present invention gives also better results as to the hiding power.

EXAMPLES

The following examples are given in order to illustrate the present invention in detail without limiting the same, in which percents are to be taken as those by weight unless otherwise indicated.

Synthetic Example 1 of Pigment Component 92.5 kg of cyanuric chloride is dispersed in about 500 kg of ice water containing 5 kg of a nonionic surfactant and maintained at at most 5° C. while stirring, to which about 134 kg of a 28% aqueous solution of ammonia was dropwise added for 2 to 3 hours. The mixture was then heated to 40° to 45° C. for about 3 hours and maintained at about 70° C. for about 30 minutes to complete the reaction. The reaction mixture was then allowed to cool and the resulting crystals are filtered at about 40° C. to obtain a filter cake of 2,4-diamino-6-chloro-1,3,5-triazine. The resulting filter cake was dispersed in water in an amount of about 10 times as much as that of the cake, to which 15 kg of ethylenediamine was added, and the mixture was reacted at a temperature of 95° to 100° C. with agitation until the alkalinity gradually disappeared. While maintaining the same temperature, an aqueous solution containing 40 kg of sodium hydroxide was dropwise added thereto for about 2 hours. pH of the reaction mixture became about 8 and the content was once dissolved and became a transparent solution, after which white crystals were shortly precipitated. The reaction mixture is further maintained at 95° to 100° C. for about 3 hours to complete the reaction and then allowed to cool. When the temperature became about 50° C., the pH of the reaction mixture was adjusted to a weak alkalinity of about pH 10 and the precipitated crystals were filtered, adequately washed with water and dried. The ethylenebismelamine obtained in this way was a white powder having MP of 314°–316° C., useful as a white pigment component.

Synthetic Examples 2 to 11 of Pigment Component

Synthetic Example 1 was repeated except using 56 kg of N,N'-dicyclohexylethylenediamine instead of 15 kg of ethylenediamine, thus obtaining N,N'-dicyclohexylethylenebismelamine. This could be recrystallized from a mixed solvent of water and methycellosolve and was a white crystal having MP of 338°–340° C., useful as a white pigment component, similar to the ethylenebismelamine.

Similarly, alkylenebismelamine derivatives as shown in Table 3 were synthesized, which were also useful as a white pigment component.

TABLE 3

| Synthetic Example No. | Substituent $-N\langle{}^{R_1}_{R_2}$ | $-N\langle{}^{R_3}_{R_4}$ | —R— | —X— | Melting Point (°C.) |
|---|---|---|---|---|---|
| 1 | —NH$_2$ | —NH$_2$ | —H | —CH$_2$CH$_2$— | 314–316 |
| 2 | —NH$_2$ | —NH$_2$ | 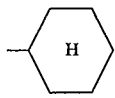 | —CH$_2$CH$_2$— | 338–340 |
| 3 | —NHCH$_3$ | —NHCH$_3$ | —H | —CH$_2$CH$_2$— | 311–312 |
| 4 | —N(CH$_3$)$_2$ | —N(CH$_3$)$_2$ | —H | —CH$_2$CH$_2$— | 308–309 |
| 5 | —N(C$_2$H$_5$)$_2$ | —N(C$_2$H$_5$)$_2$ | —H | —CH$_2$CH$_2$— | 301–303 |
| 6 | —N(C$_4$H$_9$)$_2$ | —N(C$_4$H$_9$)$_2$ | —H | —CH$_2$CH$_2$— | 298–301 |
| 7 | 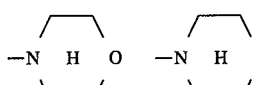 | 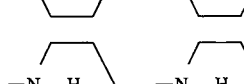 | —H | —CH$_2$CH$_2$— | >350 |
| 8 | 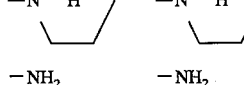 | 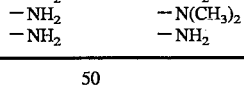 | —H | —CH$_2$CH$_2$— | >350 |
| 9 | —NH$_2$ | —NH$_2$ | —CH$_3$ | —CH$_2$CH$_2$— | 325–326 |
| 10 | —NH$_2$ | —N(CH$_3$)$_2$ | —H | —CH$_2$CH$_2$— | 311–313 |
| 11 | —NH$_2$ | —NH$_2$ | —H | —CH$_2$CH$_2$CH$_2$— | 258–259 |

Preparation Example of Ultra-fine Powder for White Pigment Composition

About 1 kg of the white powder obtained in Synthetic Example 1 was ultra-finely pulverized by means of a counter jet mill of fluidized bed type (100 AFG Pulverizer —commercial name—made by Hosokawa Micron KK) for about 1 hour to obtain an ultra-fine powder with an average grain diameter of 1–2 μm.

The ultra-fine powders used in the following Examples were prepared according to the method of this Preparation Example.

Example 1

(Preparation of Aqueous Dispersion Composition)

59 kg of water was mixed with 1 kg of a nonionic dispersing agent and 40 kg of the white pigment powder obtained in Synthetic Example 1 and then subjected to a finely pulverizing treatment using a sand grinder of a continuous and vertical type (made by Igarashi Kikai KK) to give a grain diameter of at most 1 μm and a mean grain diameter of 0.5 μm, thus obtaining an aqueous dispersion composition. This composition had a good dispersion stability.

The aqueous dispersion composition used in the following Examples was prepared according to the method of this Example 1.

Example 2

(Preparation of Oily Dispersion Composition)

45 kg of the white pigment powder obtained in Synthetic Example 2 and 15 kg of a butyral dispersion resin were added to 40 kg of ethanol and the mixture was subjected to a finely pulverizing treatment using a sand grinder of a continuous and vertical type (made by Igarashi Kikai KK) to give a mean grain diameter of 0.3 to 0.4 μm, thus obtaining a dispersion composition in an alcohol medium.

The oily dispersion composition used in the following Examples was prepared according to the method of this Example 2.

Example 3

(Coating Surface of Paper)

A coating color for a paper having a composition of the following Table 4 was prepared.

TABLE 4

Anionic Dispersant

Coating Color Composition for Paper:

| | |
|---|---|
| Ultra-fine Powder of White Pigment of Synthetic Example 1 | 100 g |
| Sodium Hexametaphopshate | 0.3 g |
| Anionic Dispersant (Aron T-40 -commercial name- made by Toa Gosei Kagaku Kogyo KK) | 0.25 g |
| Latex (JSR 0692) | 12.5 g |
| 25% Aqueous Ammonia Solution | 1.3 g |
| Water | 80 g |
| total | 194.35 g |
| (Pigment Concentration | 51.5%) |

This coating color was caoted onto a commercially available fine quality paper to give a coverage of 22 g/cm² at room temperature using Wire Rod No. 14 (commercial name) and dried at 120° C. for 1 minute. The resulting coated paper was more excellent in whiteness degree, luster and smoothness as compared with a non-coated paper.

Example 4

(Printing)

A printing paste consisting of a composition of the following Table 5 was prepared:

TABLE 5

| Printing Paste Composition | |
|---|---|
| Ultra-fine Powder of White Pigment of Synthetic Example 1 | 20 g |
| Acrylic Copolymer Binder | 80 g |
| (NK Couper A-1 -commercial name-, made by Shinnakamura Kagaku KK) | |
| total | 100 g |

The printing paste having the composition of Table 5 was printed and coated on a cotton cloth in known manner, previously dried at 100° C. for 1–2 minutes and then subjected to a heat treatment at 145° C. for 3 minutes. On the cotton cloth was obtained a clear and white print pattern, excellent in feeling as well as color fastness to washing. Similarly, clear and white printed products were obtained by printing pastes prepared using ultra-fine powders of white pigments of Synthetic Examples 2, 4 and 10.

Example 5

(Dope Dyeing of Polyesters)

1000 g of dimethyl terephthalate, 665 g of ethylene glycol, 0.55 g of manganese acetate and 0.18 g of antimony trioxide were charged in an autoclave of stainless steel, equipped with a cooler and stirrer, and heated. Release of methanol started at about 160° C. and continued for about 2.5 hours. The temperature was 225° C. at the end of the reaction. 5 g of the white pigment ultra-fine powder of Synthetic Example 1 and 0.3 g of phosphoric acid were added to this melt and the pressure in the autoclave was lowered to 1 mmHg or lower, while maintaining the temperature at 290° C., until reaching a desired degree of polymerization. The thus resulting polymer was spun by a known method in a nitrogen atmosphere at a pressure of 2 to 5 atm to obtain a polyester fiber having a higher whiteness degree and more excellent color fastness to washing and sunlight than white pigment free fibers.

Example 6

(Addition to Polyamide Resin)

1000 g of caprolactam, 30 g of water and 4 g of the ultra-fine powder of Synthetic Example 7 were stirred at 240° C. under pressure for 4 hours and heated for 60 minutes under opened state. The thus resulting polyamide melt was extruded in a belt-like form through a nozzle of slit type, rapidly cooled in water, cut into chips and dried, thus obtaining opaque polyamide chips with good whiteness degree.

In the above described procedure, when using a suitable fluorescent whitening agent, opaque polyamide chips with further high whiteness degree were obtained.

Example 7

(Addition to Polvinyl Chloride Resin 1000 g of a polyvinyl chloride forming mixture consisting of 650 g of polyvinyl chloride, 350 g of dioctyl phthalate and 2% of a stabilizer based on the polymer was mixed with 2.5% of the ultra-fine powder of Synthetic Example 11, subjected to a roller mill at 150° to 160° C. for 1 hour and extruded in a film. An opaque polyvinyl chloride film with good whiteness degree was obtained.

In the above described procedure, when adding a suitable fluorescent whitening agent, the high whiteness degree was further improved.

Example 8

(Surface Coating of Urethane Synthetic Resin Leather)

A liquid composition for a surface layer, shown in Table 6, was coated onto a mold release paper to give a coverage of 130 g/m² by means of a doctor knife and dried at 90° to 110° C. for 2 minutes. Then, onto the surface layer was coated a liquid composition for an adhesive layer, shown in Table 7, to give a coverage of 150 g/m² and further pasted basic cloth (cotton carding cloth, thickness 1 mm) through a predetermined gap of laminate rolls, followed by drying by hot air at 110° to 130° C. for 2 hours. The coated product was then aged under rolled state at 50° to 60° C. for 3 days, and after stripping the mold-release paper, was subjected to surface finishing several times by gravure rolls using a liquid composition for surface finishing, shown in Table 8, obtaining a synthetic leather prepared by coating in beautiful white.

Various CRISVONS (commercial name) and various GLOSILAC (commercial name) used in this Example were ones prepared by Dai-Nippon Ink Kagaku Kogyo KK.

TABLE 6

| Liquid Composition for Surface Layer | |
|---|---|
| CRISVON 7367 SL (urethane resin powder, solid content 35%, DMF/MEK 2:1) | 100 g |
| Ultra-fine Powder of Synthetic Example 1 | 5 g |
| MEK (methyl ethyl ketone) | 30 g |
| DMF (dimethylformamide) | 10 g |
| total | 145 g |

TABLE 7

| Liquid Composition for Adhesive Layer | |
|---|---|
| CRISVON 4010 HV (thermosetting urethane resin liquid) | 100 g |
| CRISVON NX (isocyanate type cross-linking agent) | 8 g |
| CRISVON Accel HM (crosslinking accelerator) | 3 g |
| DMF | 5 g |
| Toluene | 5 g |
| total | 121 g |

TABLE 8

| Composition for Surface Finishing | |
|---|---|
| GLOSILAC CLEAR L-0465 (surface finishing agent) | 100 g |
| GLOSILAC CLEAR MAT L-0465 (surface finishing agent) | 50 g |
| Thinner | 50 g |
| total | 200 g |

Example 9

(Addition to Gloss Paint for Drying at Normal Temperature)

A white paint for drying at normal temperature, consisting of a composition of the following Table 9, was prepared. This composition had a good stability and resistance to storage for a long time. A coating film of this composition exhibited a high luster, excellent water resisting property and alkali resisting property.

TABLE 9

| White Paint Composition for Drying at Normal Temperature | |
|---|---|
| Water | 52.5 g |
| Anionic Surfactant (Tamol 731 (25%), commercial name, made by R & H Co.) | 9.0 g |
| Nonionic Surfactant (Noigen EA 120, commercial name, made by Daiichi Kogyo Seiyaku KK) | 2.2 g |
| Ultra-fine Powder of Synthetic Example 1 | 275.0 g |
| Ethylene Glycol | 50.0 g |
| Defoaming Agent | 2.0 g |
| 28% Aqueous Ammonia | 1.0 g |

TABLE 9-continued

| White Paint Composition for Drying at Normal Temperature | |
|---|---|
| High Molecular Emulsion type Thickener (3%) | 34.8 g |
| Acryl-Styrene type Emulsion (VONCOAT EC-880 (50%), commercial name, made by Dai-Nippon Ink Kagaku Kogyo KK) | 853.8 g |
| Silicone type Resin Film-forming Aid (Texanol SC-12, commercial name, made by Chisso KK) | 60.7 g |
| total | 1341.0 g |

Example 10

(For Baking Finish)

A paint for baking finish, comprising a composition of Table 10, was prepared and sprayed and coated onto a soft steel plate of 0.8 mm in thickness by an air spray using xylene as a thinner to form a coated film (coated film 30 to 35 μm, dr). The thus coated steel was allowed to set at room temperature for 15 minutes and then subjected to a heat treatment at 130° C. for 20 minutes, thus obtaining a coated film of beautiful white, excellent in luster, hardness and alkali resistance.

| Paint Composition for Baking Finish | |
|---|---|
| Ultra-fine Powder of Synthetic Example 1 | 70 g |
| Commercial Available Coconut Oil Alkyd | 116 g |
| n-Butylated Melamine Resin | 50 g |
| total | 236 g |

The alkylenebismelamine derivative for a white pigment, represented by General Formula (I) according to the present invention, is excellent in compatibility with the above described surfactants, various additives or other organic color pigment components because of being an organic material. Accordingly, the pigment composition of the present invention has such an excellent dispersion stability and storage stability that the pigment components are hardly aggregated to cause seeding or separating during storage. Furthermore, the organic white pigment compound of the present invention is also excellent in heat resistance, which is useful for a processing carried out at a high temperature, e.g. baking finish or dope dyeing of various polymers.

As described above, the alkylenebismelamine derivative for a organic white pigment according to the present invention has broad applications, for example, coating agents of papers, aqueous or oily paints for various coatings, printing inks, pigments for oil colors or crayons, pigments for printing or dope dyeing of polymers.

What is claimed is:

1. An alkylenebismelamine derivative represented by the following formula (I):

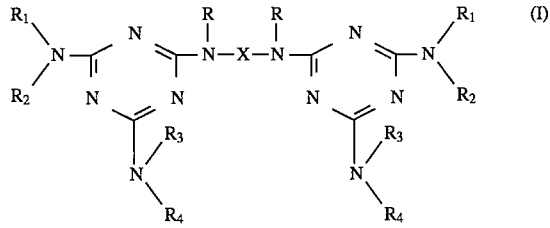

wherein

X is an alkylene group containing 2 to 3 carbon atoms;

R is cyclohexyl;

R₁ and R₂ are each lower alkyl containing 1 to 4 carbon atoms, or R₁ and R₂ combine with an adjacent N atom to form a piperidino or morpholino group; and R₃ and R₄ are each lower alkyl containing 1 to 4 carbon atoms, or R₃ and R₄ combine with an adjacent N atom to form a piperidino or morpholino group.

2. An alkylenebismelamine derivative according to claim 1, wherein R₁, R₂, and an adjacent N combine and R₃, R₄, and an adjacent N combine each to form piperidino group.

3. An alkylenebismelamine derivative represented by the following formula (I):

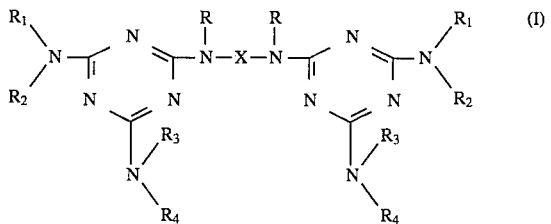

wherein

X is an alkylene group containing 2 to 3 carbon atoms;

R is selected from the group consisting of hydrogen, lower alkyl containing 1 to 4 carbon atoms, and cyclohexyl;

R₁, R₂ R₃, and R₄ are each butyl or R₁ and R₂ combine with an adjacent N atom to form piperidino, and R₃ and R₄ are each butyl or combine with an adjacent N atom to form piperidino.

4. An alkylenebismelamine derivative selected from the group consisting of N,N'-bis-(4,6-bis-morpholino-1,3,5-triazinyl-2)-ethylenediamine and N,N'-bis-(4,6-bis-piperidino-1,3,5-triazinyl-2)-ethylenediamine.

* * * * *